(12) United States Patent
Miwa et al.

(10) Patent No.: US 7,361,258 B2
(45) Date of Patent: Apr. 22, 2008

(54) SENSOR ELEMENT AND GAS SENSOR

(75) Inventors: Kaname Miwa, Aichi (JP); Katsuhiko Horii, Aichi (JP); Hideaki Yagi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/313,184

(22) Filed: May 18, 1999

(65) Prior Publication Data

US 2003/0136676 A1 Jul. 24, 2003

(30) Foreign Application Priority Data

May 18, 1998 (JP) .................................. 10-153612

(51) Int. Cl.
*G01N 27/407* (2006.01)
*G01N 27/41* (2006.01)

(52) U.S. Cl. ...................... 204/425; 204/424; 204/426; 204/429

(58) Field of Classification Search ......... 204/421–429
See application file for complete search history.

(56) References Cited

U.S. PATENT DOCUMENTS

| | | | |
|---|---|---|---|
| 4,502,939 A * | 3/1985 | Holfelder et al. ............ 204/429 |
| 4,563,249 A * | 1/1986 | Hale .......................... 205/793 |
| 4,657,659 A * | 4/1987 | Mase et al. .................. 204/426 |
| 4,668,374 A * | 5/1987 | Bhagat et al. ............... 204/412 |
| 4,668,375 A | 5/1987 | Kato et al. ................... 204/426 |
| 4,724,061 A * | 2/1988 | Nyberg ....................... 204/426 |
| 5,139,639 A | 8/1992 | Holleboom |
| 5,174,885 A | 12/1992 | Hayakawa et al. ......... 204/425 |
| 5,348,630 A | 9/1994 | Yagi et al. ............. 204/153.22 |
| 5,403,452 A * | 4/1995 | Hielscher et al. ........... 204/426 |
| 5,672,811 A | 9/1997 | Kato et al. .................. 73/31.05 |
| 5,676,811 A * | 10/1997 | Makino et al. .............. 204/425 |
| 5,716,506 A * | 2/1998 | Maclay et al. .............. 204/424 |
| 5,810,997 A * | 9/1998 | Okazaki et al. .......... 205/784.5 |
| 6,036,841 A * | 3/2000 | Kato et al. |
| 6,254,750 B1 * | 7/2001 | Patrick et al. |
| 6,344,134 B1 * | 2/2002 | Yamada et al. |

FOREIGN PATENT DOCUMENTS

| | | | |
|---|---|---|---|
| DE | 39 38 056 A1 | | 5/1990 |
| EP | 0 791 828 A1 | | 8/1997 |
| EP | 0 810 430 | * | 12/1997 |
| GB | 2311377 A | * | 9/1997 |

(Continued)

*Primary Examiner*—Kaj K. Olsen
(74) *Attorney, Agent, or Firm*—Sughrue Mion, PLLC

(57) ABSTRACT

A flat limiting-current sensor 10 includes a solid electrolyte substrate 22, a negative electrode 34a and a positive electrode 32a. The negative and positive electrodes 34a and 32a, respectively, are disposed on the same side of the solid electrolyte substrate 22. A voltage of 0.8 V is applied between the negative electrode 34a and the positive electrode 32a in order to determine oxygen concentration. The ratio between the area of the negative electrode 34a and the area of the positive electrode 32a is set to 1:2, thereby reducing element resistance to 74% that of the case where the negative electrode and the positive electrode assume the same area. Thus, the measurement accuracy of the flat limiting-current sensor 10 is improved.

6 Claims, 12 Drawing Sheets

FOREIGN PATENT DOCUMENTS

| | | |
|---|---|---|
| JP | 57-154050 | 9/1982 |
| JP | 61-97754 | 6/1986 |
| JP | 2-147853 | 6/1990 |
| JP | 4-5562 | 1/1992 |
| JP | 5-60725 | 3/1993 |
| JP | 5-87773 | 4/1993 |
| JP | 5-312768 | 11/1993 |
| JP | 5-332985 | 12/1993 |
| JP | 8-201337 | 8/1996 |
| JP | 10-38845 | 2/1998 |
| JP | 63-26568 | 2/1998 |
| JP | 2-147854 | 6/1999 |
| WO | WO 95/14226 | 5/1995 |

\* cited by examiner

Fig.5A.

0.7 V APPLIED

| (NEGATIVE ELECTRODE) : (POSITIVE ELECTRODE) | 6:1 | 5:1 | 4:1 | 3:1 | 2:1 | 1:1 | 1:2 | 1:3 | 1:4 | 1:5 | 1:6 |
|---|---|---|---|---|---|---|---|---|---|---|---|
| CURRENT (μA) | 78.4 | 93.11 | 114.1 | 116.7 | 85.6 | 80.4 | 109.4 | 120.1 | 130.1 | 111.0 | 82.3 |
| ELEMENT RESISTANCE (kΩ) | 8.93 | 7.52 | 6.13 | 6.00 | 8.18 | 8.70 | 6.40 | 5.83 | 5.38 | 6.31 | 8.51 |

Fig.5B.

1.8V APPLIED

| (NEGATIVE ELECTRODE) : (POSITIVE ELECTRODE) | 6:1 | 5:1 | 4:1 | 3:1 | 2:1 | 1:1 | 1:2 | 1:3 | 1:4 | 1:5 | 1:6 |
|---|---|---|---|---|---|---|---|---|---|---|---|
| CURRENT (μA) | 264.4 | 403.7 | 466.7 | 461.3 | 315.4 | 255.8 | 283.9 | 297.5 | 331.4 | 312.4 | 232.6 |
| ELEMENT RESISTANCE (kΩ) | 7.31 | 4.46 | 3.86 | 3.90 | 5.70 | 7.03 | 6.34 | 6.05 | 5.43 | 5.76 | 7.74 |

SENSOR ELEMENT AND GAS SENSOR

FIELD OF THE INVENTION

The present invention relates to a gas sensor for sensing gas, such as oxygen ($O_2$), carbon dioxide ($CO_2$), carbon monoxide (CO), water ($H_2O$), hydrocarbon (e.g., $CH_4$, $C_2H_6$ or $C_3H_8$), nitrogen oxide (NOx), or sulfur oxide (SOx), and more particularly to a flat limiting-current-type sensor and an oxygen-containing gas component sensor in which negative and positive electrodes are disposed on the same side of a solid electrolyte substrate, and the concentration of a particular gas contained in a gas to be measured (hereinafter referred to as "measurement gas") is determined through the restriction of gas diffusion to the negative electrode.

BACKGROUND OF THE INVENTION

FIG. 12A shows a sectional view of an oxygen sensor for determining the oxygen concentration of a measurement gas. A pair of electrodes 132 and 134 formed from, for example, porous platinum and having the form of a thick or thin film are formed on opposite sides of an oxygen-ion conductive solid electrolyte substrate 122. A voltage is applied between the electrodes 132 and 134 and a resultant current is measured in order to determine an oxygen concentration. According to the configuration of FIG. 12A, a housing 124 having a small oxygen diffusion hole 234C formed therein covers the negative electrode 134 so as to limit diffusion of oxygen through the oxygen diffusion hole 234C, so that a value of current proportional to oxygen concentration is obtained. Such an oxygen sensor must be provided with a heater for heating a solid electrolyte substrate to a temperature of about 400° C. to 900° C. in order to activate the solid electrolyte substrate. However, since the opposite sides of the solid electrolyte substrate bear respective electrodes, attachment of the heater to the oxygen sensor is difficult.

To solve the above problem, a flat limiting-current-type sensor as shown in FIG. 12B is used. As shown in FIG. 12B, a negative electrode 134 and a positive electrode 132 are disposed on the same side of the solid electrolyte substrate 122. Since the electrodes 132 and 134 are disposed on the same side of the solid electrolyte substrate 122, the flat limiting-current-type sensor has an advantage in that a heater can be readily disposed on the other side of the solid electrolyte substrate 122. The configuration of the flat limiting-current-type sensor is described in detail in Japanese Patent Application Laid-open (kokai) No. 2-147853 which corresponds to U.S. Pat. No. 5,348,630 filed by the present applicants.

FIG. 12C shows the flat limiting-current-type sensor of FIG. 12B as viewed in the direction of arrow C of FIG. 12B, i.e., FIG. 12C shows a side view of the flat limiting-current-type sensor. Since the negative electrode 134 and the positive electrode 132 are disposed on the same side of the solid electrolyte substrate 122, the area of the negative electrode 134 (positive electrode 132) is subsequently half that in the case of the limiting-current-type sensor of FIG. 12A. Accordingly, the flat limiting-current-type sensor of FIG. 12B has a problem in that an element resistance becomes higher and that measurement accuracy becomes poorer, as compared to the sensor of FIG. 12A.

In view of the foregoing, an object of the present invention is to provide a flat limiting-current-type sensor having an improved measurement accuracy for a given device size.

The present inventors realized that, in a sensor element, a negative electrode and a positive electrode might not operate in a similar manner. The flat limiting-current-type sensor repeats an oxygen-related pumping cycle. Specifically, oxygen is pumped into a solid electrolyte substrate in the form of ions at the interface between the solid electrolyte substrate and the porous negative electrode. The pumped-in oxygen ions are transmitted through the solid electrolyte substrate. Then, the transmitted oxygen ions are pumped out in the form of oxygen at the interface between the solid electrolyte substrate and the porous positive electrode. The present inventors assumed that there might be a difference between the readiness of reaction for pumping in oxygen in the form of ions and the readiness of reaction for pumping out oxygen ions in the form of oxygen. Specifically, according to assumption of the inventors, in a conventional flat limiting-current-type sensor as shown in FIG. 12C, the area of the negative electrode is equal to that of the positive electrode; consequently, transmission of ions is controlled by the negative electrode or the positive electrode, whichever is lower in terms of readiness for reaction, with a resultant increase in element resistance. The inventors conducted experiment on the basis of the assumption and obtained an appropriate area ratio between the negative electrode and the positive electrode.

SUMMARY OF THE INVENTION

Accordingly, the present invention provides a sensor element comprising negative and positive electrodes disposed on the same side of a solid electrolyte substrate, wherein the area of said negative electrode differs from the area of said positive electrode.

Advantageously, this can be used to lower the element resistance of the flat limiting-current-type sensor, thus improving measurement accuracy or S/N ratio.

Preferably, the area of the negative electrode and the area of the positive electrode differ by at least twofold, thereby lowering the element resistance of a flat limiting-current-type sensor and thus improving measurement accuracy.

Preferably in a sensor for determining a gas concentration through application of an electric potential of 0.2 V to 1.1 V, the ratio between the area of the negative electrode and the area of the positive electrode is set within a range of 2:1 to 5:1, thereby enabling the element resistance to be reduced to 94% to 86% of that in the case where the negative electrode and the positive electrode assume the same area. As a result, the measurement accuracy of a flat limiting-current-type sensor can be improved.

Preferably in a sensor for determining a gas concentration through application of an electric potential of 0.2 V to 1.1 V, the ratio between the area of the negative electrode and the area of the positive electrode is set within a range of 1:2 to 1:5, thereby enabling the element resistance to be reduced to 74% to 73% of that in the case where the negative electrode and the positive electrode assume the same area. As a result, the measurement accuracy of a flat limiting-current-type sensor can be improved.

Preferably in a sensor for determining a gas concentration through application of an electric potential of 1.1 V to 2.5 V, the ratio between the area of the negative electrode and the area of the positive electrode is set within a range of 1:2 to 1:5, thereby enabling the element resistance to be reduced to 90% to 82% of that in the case where the negative electrode and the positive electrode assume the same area. As a result, the measurement accuracy of a flat limiting-current-type sensor can be improved.

Preferably in a sensor for determining a gas concentration through application of an electric potential of 1.1 V to 2.5 V, the ratio between the area of the negative electrode and the area of the positive electrode is set within a range of 2:1 to 5:1, thereby enabling the element resistance to be reduced to 81% to 63% of that in the case where the negative electrode and the positive electrode assume the same area. As a result, the measurement accuracy of a flat limiting-current-type sensor can be improved.

These and other objects and advantages of the invention will be apparent upon reference to the following specification, claims and drawings.

BRIEF DESCRIPTION OF THE DRAWINGS

FIG. 2 shows views of the flat limiting-current-type sensor of FIG. 1, wherein

FIG. 5 gives tables showing the test results of flat limiting-current-type sensor samples having different area ratios between a negative electrode and a positive electrode, wherein FIG. 5A is a table showing element resistance values as measured when a voltage of 0.7 V is applied to each of the samples, and FIG. 5B is a table showing element resistance values as measured when a voltage of 1.8 V is applied to each of the samples;

FIG. 8 including

FIG. 11 shows views of a sensor according to a third embodiment of the present invention, wherein FIG. 12 shows views of conventional sensors, wherein

Figure 1:
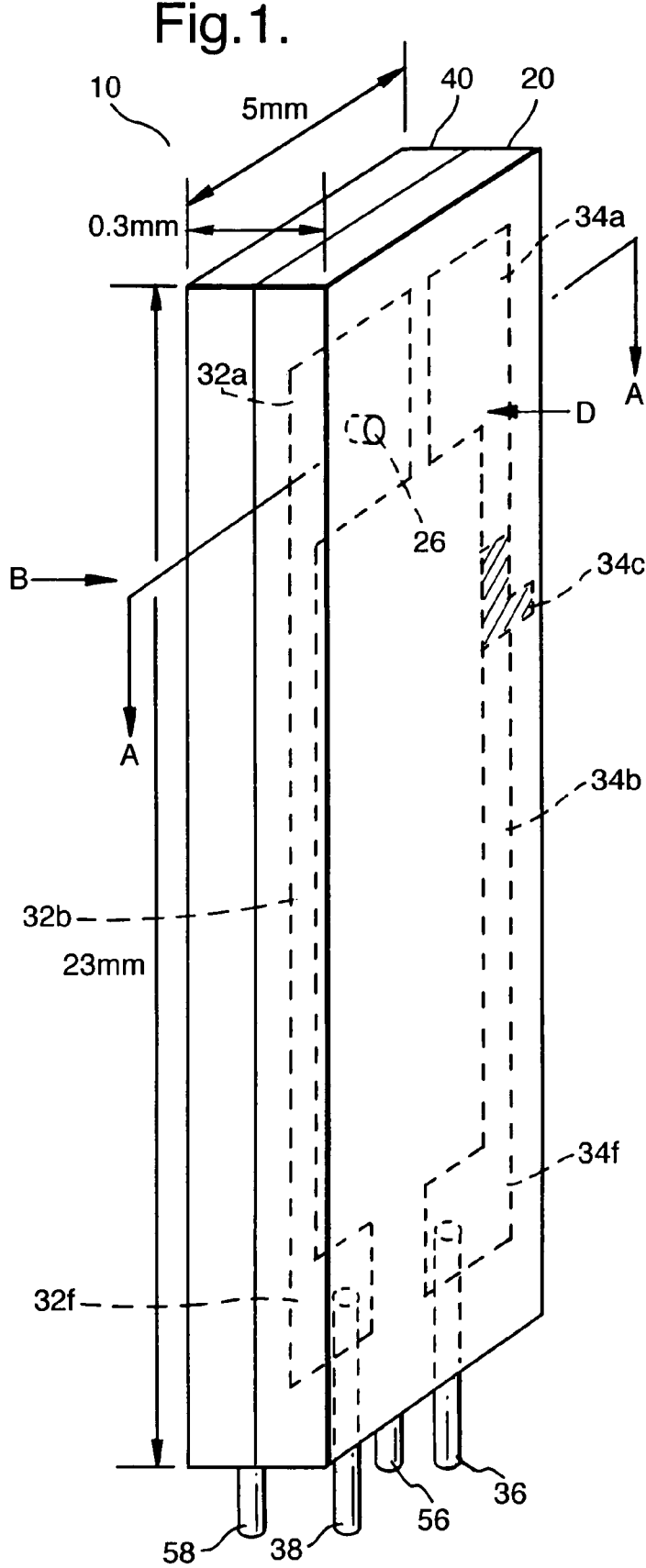
FIG. 1 is a perspective view of a flat limiting-current-type sensor according to a first embodiment of the present invention as viewed from the front side of the sensor.

In the accompanying drawings, the following reference numerals denote the items listed below.

10: flat limiting-current-type sensor
20: sensor element
22: solid electrolyte substrate
24: solid electrolyte substrate
26: gas outlet hole
32a: positive electrode
34a: negative electrode
34c: gas diffusion portion
40: ceramic heater

PREFERRED EMBODIMENTS

Figure 2A:
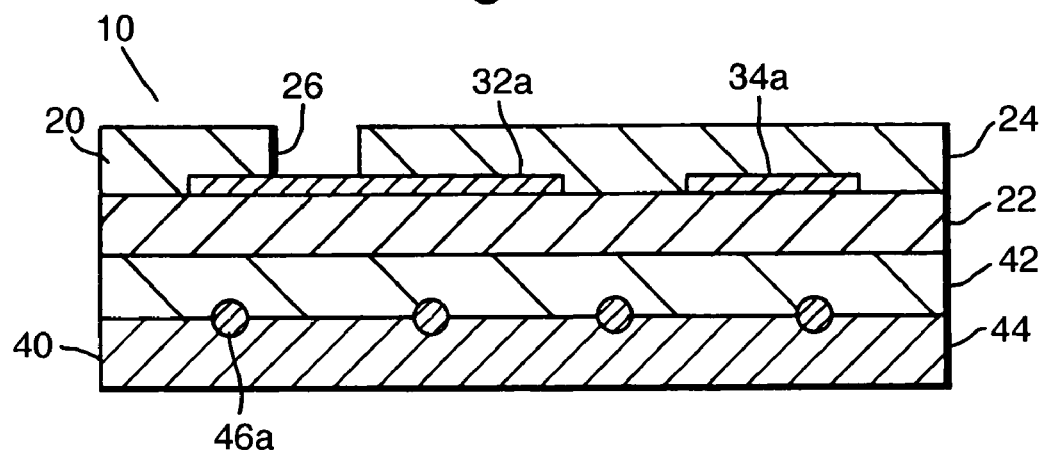
FIG. 2A is a sectional view taken along line A-A of FIG. 1.
Figure 2B:
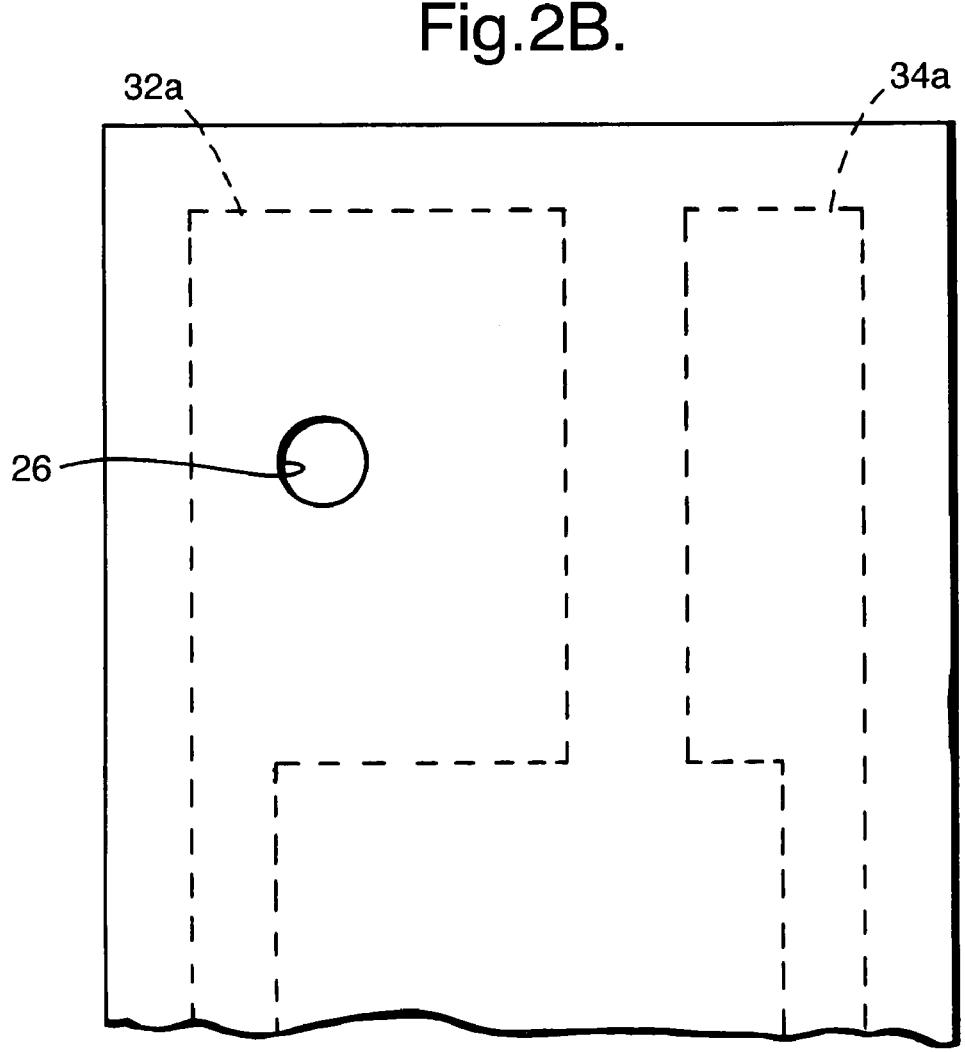
FIG. 2B is a view as viewed in the direction of arrow D of FIG. 1.

FIG. 1 shows a flat limiting-current-type sensor 10 of the first embodiment serving as an oxygen sensor. FIG. 2A is a sectional view of the flat limiting-current-type sensor of FIG. 1 taken along line A-A of FIG. 1. FIG. 2B is a side view of the flat limiting-current-type sensor of FIG. 1 as viewed in the direction of arrow D of FIG. 1 (as viewed from the front side). The flat limiting-current-type sensor 10 includes a sensor element 20 for measuring oxygen concentration and a ceramic heater 40 for heating the sensor element to a temperature of 500° C. to 600° C. The sensor element 20 and the ceramic heater 40 are bonded together by means of glass. The flat limiting-current-type sensor 10 measures 0.3 mm (thickness)×5 mm (width)×23 mm (height).

As shown in FIG. 2A, the sensor element 20 includes solid electrolyte substrates 22 and 24 formed from zirconia, which exhibits good conductance of oxygen ions; a positive electrode 32a formed from porous platinum; a lead portion 32b (see FIG. 1) for supplying current to the positive electrode 32a; a connection electrode 34f connected to a platinum wire 36; a negative electrode 34a formed from porous platinum; a lead portion 34b for supplying current to the negative electrode 34a; a connection electrode 32f connected to a platinum wire 38; a gas diffusion portion 34c extending sideward from the lead portion and adapted to introduce an ambient gas into the negative electrode 34a; and a gas outlet hole 26 for releasing oxygen from the positive electrode 32a to the exterior of the sensor element 20. The negative electrode 34a and the positive electrode 32a assume a thickness of about 20 μm.

According to the present embodiment, the gas diffusion portion 34c formed from porous platinum extends from the lead portion 34b to the periphery of the sensor element 20 so as to supply a gas containing oxygen to the negative electrode 34a under a diffusion resistance. Instead of being formed from porous platinum having porosity for diffusion resistance, the gas diffusion portion 34c may assume the form of a small hole for supplying oxygen to the negative electrode 34a.

Figure 3:
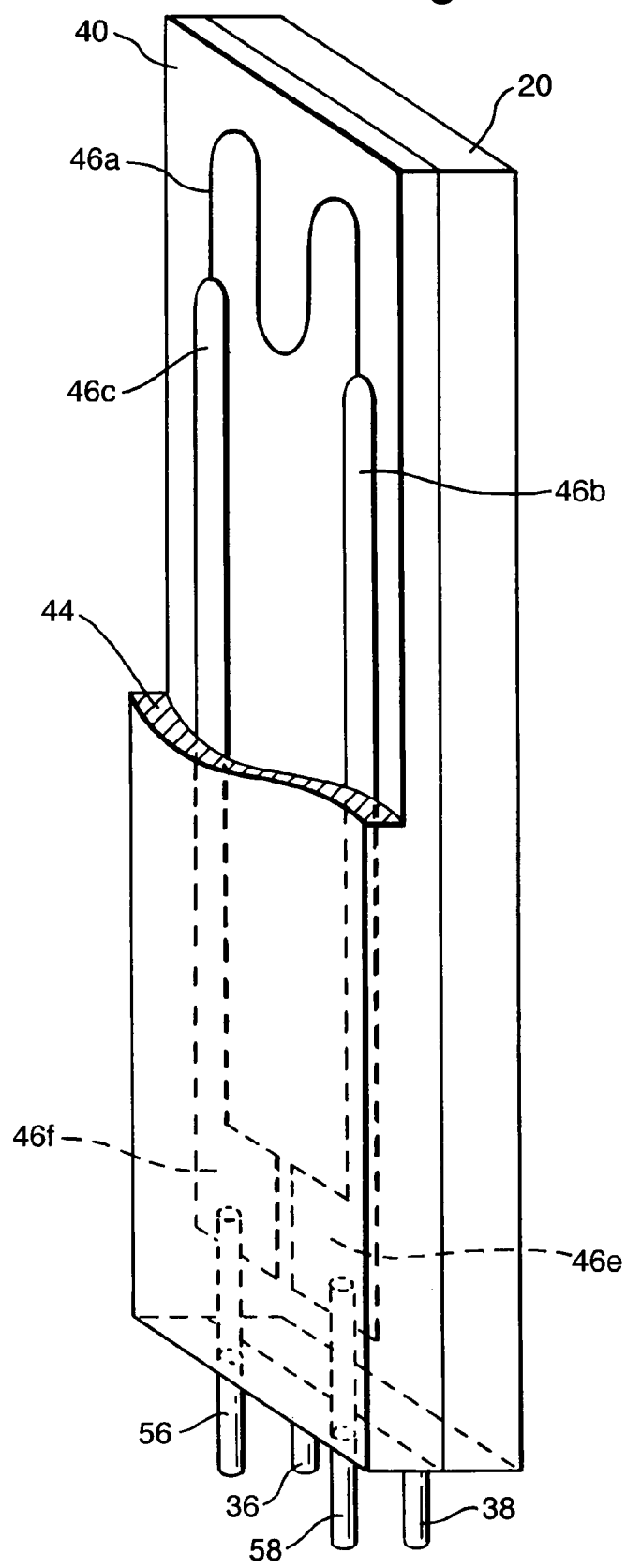
FIG. 3 is a perspective view of the flat limiting-current-type sensor of the first embodiment as viewed from the back side of the sensor.

FIG. 3 is a side view of the flat limiting-current-type sensor of FIG. 1 as viewed in the direction of arrow B of FIG. 1 (as viewed from the back side). In FIG. 3, the ceramic heater 40 is partially broken. As shown in FIGS. 3 and 2A, the ceramic heater 40 includes an alumina substrate 42 and an alumina substrate 44, both of which have an external size identical to that of the sensor element 20. The ceramic heater 40 further includes a heater electrode (heat-generating portion) 46a having a narrow width and assuming a substantially M-shaped form; heater electrodes (lead portions) 46b and 46c having a wide width; and heater connection electrodes 46d and 46e connected to platinum wires 56 and 58, respectively. All of these elements are sandwiched between the alumina substrates 42 and 44. When current flows to the thin heater electrode (heat-generating portion) 46a via the platinum wires 56 and 58, the heater electrode 46a generates heat to thereby heat to a temperature of about 550° C. a tip portion of the sensor element 20 where the negative electrode 34a and the positive electrode 32a, which have been described with reference to FIG. 1, are disposed.

Figure 4:
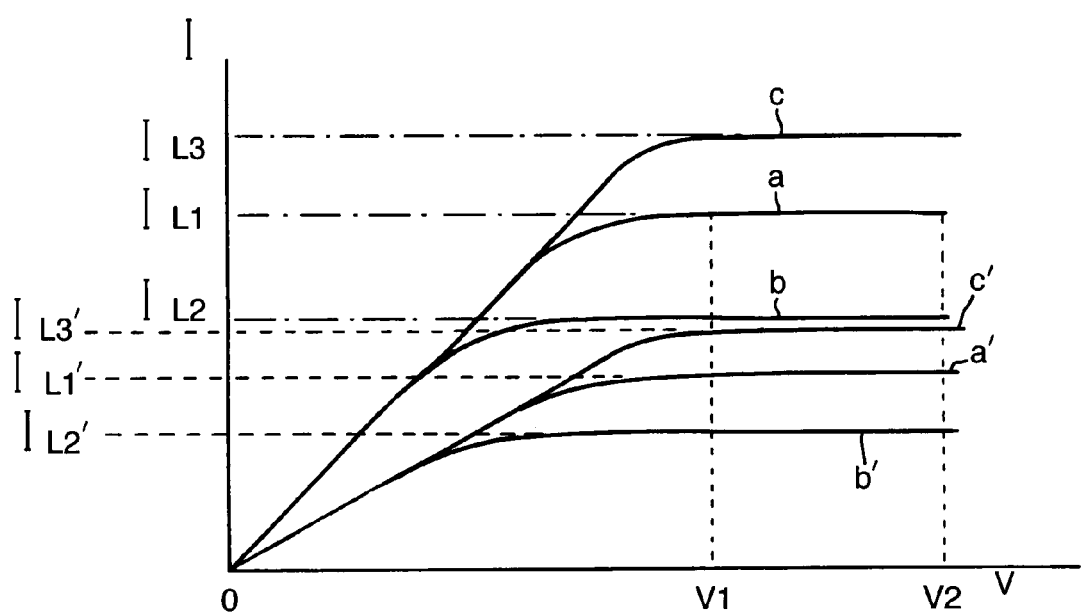
FIG. 4 is a graph showing voltage-current characteristics of the flat limiting-current-type sensor of the first embodiment.

The operational principle of the flat limiting-current-type sensor 10 with reference to the graph of FIG. 4 showing the relationship between an applied voltage and current in the sensor element 20.

The flat limiting-current-type sensor 10 is placed in an atmosphere of a certain oxygen concentration. Current is supplied to the ceramic heater 40 so as to heat the sensor element 20 (solid electrolyte substrate 22) to an ion conduction temperature (activation temperature: about 500° C. to 600° C.). Under the circumstance, when voltage is applied between the negative electrode 34a and the positive electrode 32a via the platinum wires 36 and 38, oxygen molecules introduced via the gas diffusion portion 34c are charged at the interface between the negative electrode 34a and the solid electrolyte substrate 22 and are thus ionized. Oxygen ions are taken into and transmitted through the solid electrolyte substrate 22. The thus-transmitted oxygen ions are caused to discharge at the interface between the solid electrolyte substrate 22 and the positive electrode 32a, thereby returning to oxygen molecules. The thus-formed oxygen is discharged through the gas outlet hole 26. In other words, oxygen is pumped between the negative electrode 34a and the positive electrode 32a, so that current flows through the sensor element 20.

When voltage applied to the sensor element 20 is increased from 0 to V1 as represented by curve a of FIG. 4, the amount of oxygen pumped from the negative electrode 34a to the positive electrode 32a increases. During the pumping period, the amount of oxygen taken in via the gas diffusion portion 34c and the amount of oxygen discharged through the gas outlet hole 26 are relatively small. As a result, as represented by curve a of FIG. 4, the amount of oxygen pumped, thus current, increases with the applied voltage.

When the voltage applied to the sensor element 20 is increased from V1 to V2, the amount of oxygen introduced via the gas diffusion portion 34c of porous platinum is limited to a predetermined value (IL1). Specifically, since the amount of oxygen introduced via the gas diffusion portion 34c is limited, even when the voltage applied to the sensor element 20 is increased from V1 to V2, current flowing through the sensor element 20 is maintained at a constant value of IL1. Curve b corresponds to the case of low oxygen concentration in an atmosphere to be measured. In the case of low oxygen concentration, current flowing through the sensor element 20 assumes a constant value of IL2 lower than IL1. Current c corresponds to the case where an atmosphere to be measured has oxygen concentration higher than that in the case of curve a. In the case of high oxygen concentration, current flowing through the sensor element 20 assumes a constant value of IL3 higher than IL1. On the basis of the differential between these constant values of current, oxygen concentration is determined.

In the case of an element having a high resistance, even when the voltage is increased from V1 to V2, current flowing through the element does not become constant as represented by curves a, b and c, since the amount of oxygen introduced via the gas diffusion portion 34c does not reach an upper limit which the gas diffusion portion 34c establishes with respect to the amount of oxygen introduced. Thus, a diffusion rate as observed at a gas introduction portion must be reduced (the size of a single hole must be decreased or the porosity of the porous portion must be decreased) so as to decrease the upper limit. In FIG. 4, curves a', b' and c' show voltage-current characteristics of a flat limiting-current-type sensor which has a high V/I value, i.e., a high element resistance and in which the amount of diffusion of oxygen is decreased at the gas introduction portion. Curve a' is obtained through measurement conducted at oxygen concentration identical to that as employed in the case of curve a. Curve b' is obtained through measurement conducted at oxygen concentration (low concentration) identical to that as employed in the case of curve b. Curve c' is obtained through measurement conducted at oxygen concentration (high concentration) identical to that as employed in the case of curve c. As seen from FIG. 4, the differential between constant values of current IL1', IL2' and IL3' as observed with the flat limiting-current-type sensor of a high element resistance is smaller than the differential between constant values of current IL1, IL2 and IL3 as observed with the aforementioned flat limiting-current-type sensor of a low element resistance. This indicates that an increase in element resistance causes an impairment in measurement accuracy.

Figure 12A:
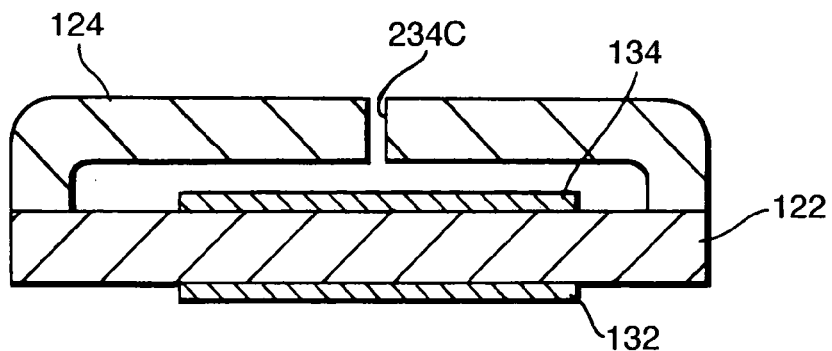
FIG. 12A is a sectional view of a conventional limiting-current-type sensor.
Figure 12B:
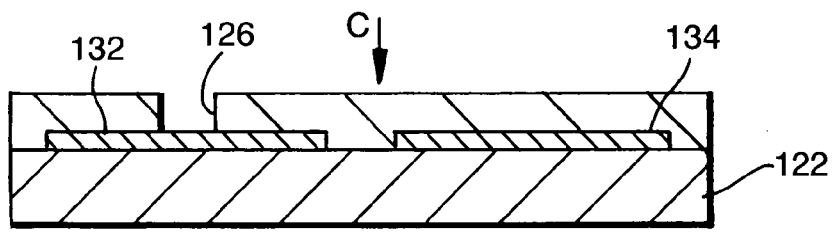
FIG. 12B is a sectional view of a conventional flat limiting-current-type sensor.
Figure 12C:
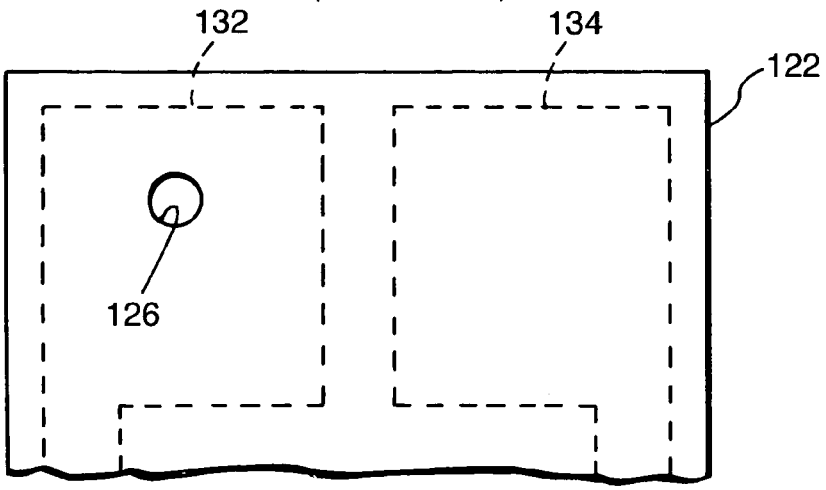
FIG. 12C is a side view of the conventional flat limiting-current-type sensor.

As shown in FIGS. 1, 2A, and 2B, in the first limiting-current-type sensor 10 of the first embodiment, the area ratio between the positive electrode 32a and the negative electrode 34a is set to 2:1. As a result, element resistance is reduced, as will be described later, to 74% that of the conventional flat limiting-current-type sensor which has been described above with reference to FIGS. 12B and 12C and in which the negative electrode 132 and the positive electrode 134 assume the same area. Thus, measurement accuracy is improved accordingly.

In the flat limiting-current-type sensor of the first embodiment serving as an oxygen sensor, a voltage of 0.7 V is applied between the negative electrode 34a and the positive electrode 32a. Thus, the area ratio between the positive electrode 32a and the negative electrode 34a is set to 2:1, thereby reducing element resistance. Element resistance was experimentally measured with respect to different area ratios between the negative electrode 34a and the positive electrode 32a. The test results will be described with reference to FIGS. 5A and 6.

The test used the flat limiting-current-type sensor 10 of the first embodiment, which has been described above with reference to FIGS. 1 to 3. Specifically, while the sum of the areas of the negative and positive electrodes 34a and 32a, respectively, was held constant, the area of the negative electrode 34a and the area of the positive electrode 32a were varied for measurement of element resistance. Test samples assumed the following area ratios of (area of negative electrode 34a):(area of positive electrode 32a): 6:1; 5:1; 4:1; 3:1; 2:1 (flat limiting-current-type sensor of first embodiment); 1:1 (conventional flat limiting-current-type sensor shown in FIG. 12); 1:2 (flat limiting-current-type sensor of second embodiment, which will be described later); 1:3; 1:4; 1:5; and 1:6. Each of the test samples was heated to a sensor element temperature of 600° C. by means of a heater. The test samples were placed in a thermostat-hygrostat chamber maintained at 60° C. and 60% RH. A voltage of 0.7 V and 1.8 V was applied between the negative electrode 34a and the positive electrode 32a with respect to each of the test samples. During application of the voltage, current flowing through each of the test samples was measured. Element resistance was calculated from the measured current value.

A voltage of 0.7 V was selected to represent an electric potential which ranges from 0.2 V to 0.8 V and which is applied to a flat limiting-current-type sensor serving as an oxygen sensor. Notably, a voltage of 0.7 V is considered as a representative for an electric potential ranging from 0.2 V to 1.1 V. A voltage of 1.8 V was selected to represent an electric potential which ranges from 1.1 V to 2.5 V and which is applied to a flat limiting-current-type sensor serving as a humidity sensor.

Figure 6:
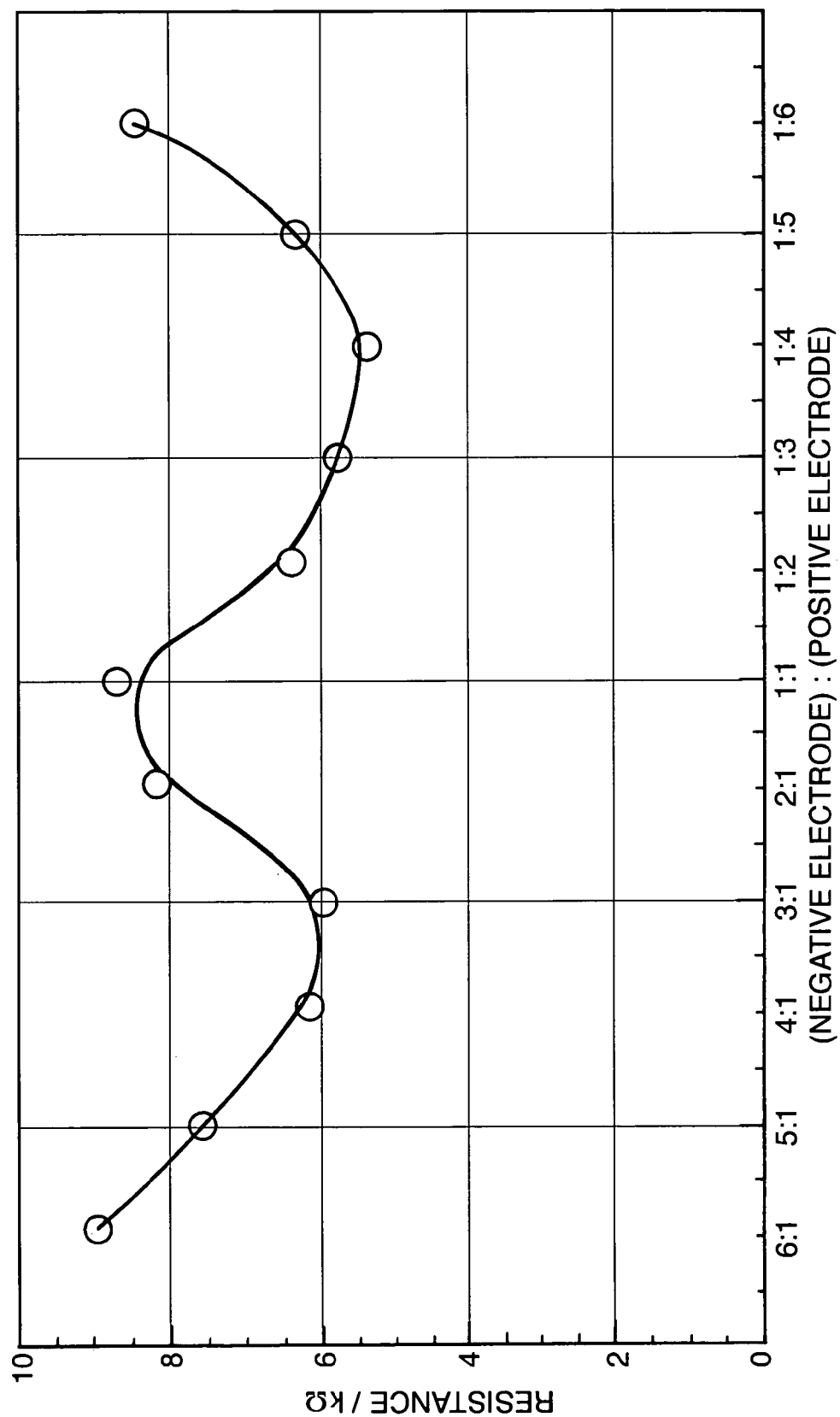
FIG. 6 is a graph depicting data of FIG. 5A.

FIG. 5A shows current values as measured when a voltage of 0.7 V is applied to the above test samples and element resistance values calculated from the measured current values. FIG. 6 is a graph depicting the measurements of FIG. 5A.

When the ratio between the area of the negative electrode and the area of the positive electrode is set within a range of 2:1 to 5:1, element resistance assumes a value of 8.18 kΩ to 7.52 kΩ, which is 94% to 86% that in the case where the negative electrode and the positive electrode assume the same area (1:1; element resistance 8.70 kΩ) When the ratio between the area of the negative electrode and the area of the positive electrode is set within a range of 1:2 to 1:5, element resistance assumes a value of 6.40 kΩ to 6.31 kΩ, which is 74% to 73% that (8.70 kΩ) in the case where the negative electrode and the positive electrode assume the same area. Thus, when the flat limiting-current-type sensor is used as an oxygen sensor, i.e., when a voltage of 0.7 V is applied thereto, through employment of a ratio of 1:2 to 1:5 between the area of the negative electrode and the area of the positive electrode, element resistance can be significantly reduced. Particularly, at a ratio of 1:3 to 1:4, element resistance assumes a minimum value of 5.83 kΩ to 5.38 kΩ.

Before the above experiment was conducted, the present inventors had foreseen that element resistance would be reduced by making the area of the negative electrode 34a greater or smaller than that of the positive electrode 32a. However, as seen from the above test results, element resistance can be reduced in either case of making the area of the negative electrode 34a greater or smaller than that of the positive electrode 32a. A conceivable reason is that pumping of oxygen between the positive electrode 32a and the negative electrode 34a is controlled by a plurality of parameters, not by a single parameter. As seen from the above test results, element resistance can be reduced by making the size of the negative electrode 34a differ from that of the positive electrode 32a. Particularly, when the flat limiting-current-type sensor is used as, e.g., an oxygen sensor, wherein a relatively low voltage of about 0.7 V is applied thereto, element resistance can be significantly reduced by making the size of the positive electrode 32a greater than that of the negative electrode 34a.

Figure 7:
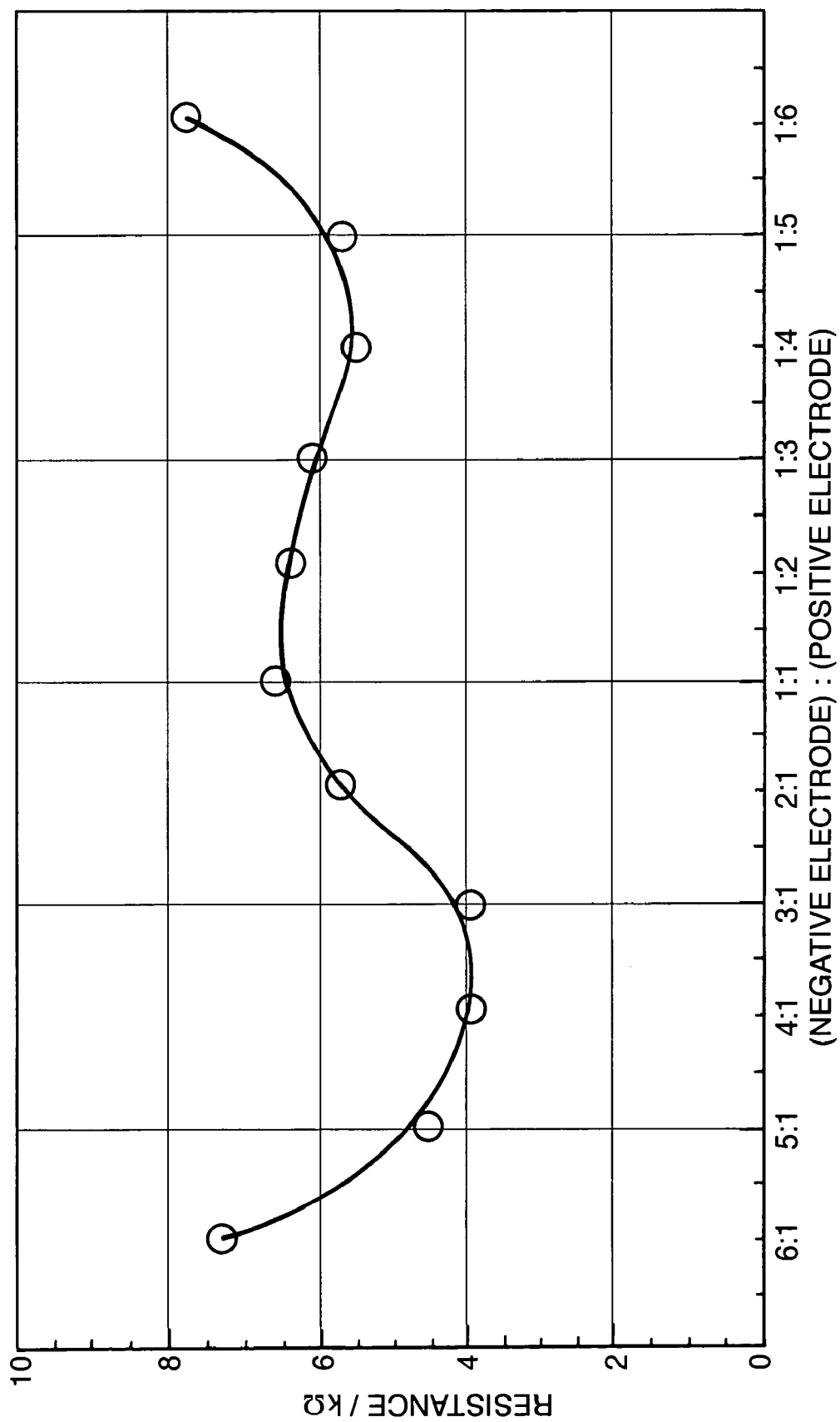
FIG. 7 is a graph depicting data of FIG. 5B.

FIG. 5B shows current values as measured when a voltage of 1.8 V is applied to the above test samples and element resistance values calculated from the measured current values. FIG. 7 is a graph depicting the measurements of FIG. 5B.

When the ratio between the area of the negative electrode and the area of the positive electrode is set within a range of 2:1 to 5:1, element resistance assumes a value of 5.70 kΩ to 4.46 kΩ, which is 81% to 63% that in the case where the negative electrode and the positive electrode assume the same area (1:1; element resistance 7.03 kΩ). When the ratio between the area of the negative electrode and the area of the positive electrode is set within a range of 1:2 to 1:5, element resistance assumes a value of 6.34 kΩ to 5.76 kΩ, which is 90% to 82% that in the case where the negative electrode and the positive electrode assume the same area. Thus, when the flat limiting-current-type sensor is used as, e.g., a humidity sensor, wherein a voltage of 1.8 V is applied thereto, through employment of a ratio of 2:1 to 5:1 between the area of the negative electrode and the area of the positive electrode, element resistance can be significantly reduced. Particularly, at a ratio of 3:1 to 4:1, element resistance assumes a minimum value of 3.90 kΩ to 3.86 kΩ. Notably, a characteristic as observed when a voltage of 1.8 V is applied is reverse to that as observed when a voltage of 0.7 V is applied, which has been described above with reference to FIG. 5A and FIG. 6.

Next, a method for fabricating the flat limiting-current-type sensor of the first embodiment will be described. First, a process for fabricating the sensor element 20 will be described with reference to FIG. 8.

First, a solid electrolyte green sheet 22a (FIG. 8A) for forming the solid electrolyte substrate 22 and a solid electrolyte green sheet 24a (FIG. 8B) for forming the solid electrolyte substrate 24 are formed from a material which contains zirconium oxide as a main component and yttrium oxide added. A through-hole 26 is formed in the solid electrolyte green sheet 24a. The through-hole 26 will become the gas outlet hole 26 through exposure to firing.

Figure 8A:
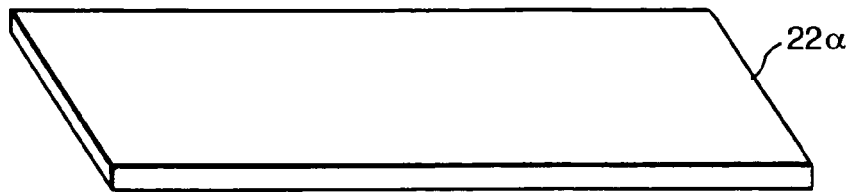
FIGS. 8A, 8B, 8C, 8D and 8E are views showing a process for fabricating a sensor element of the flat limiting-current-type sensor.
Figure 8B:
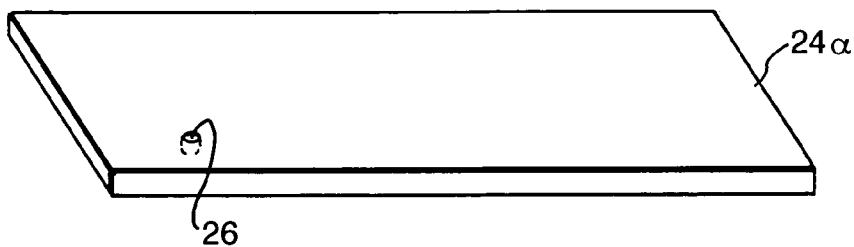
Figure 8C:
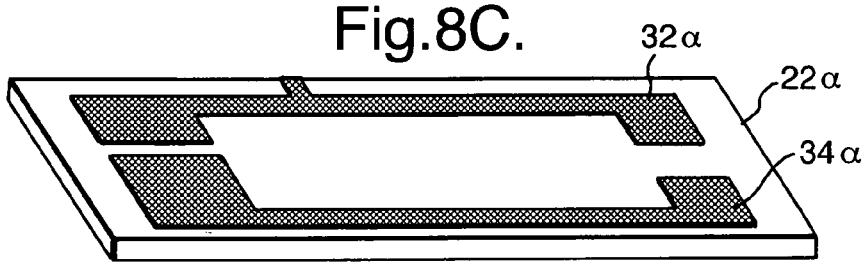
Figure 8D:
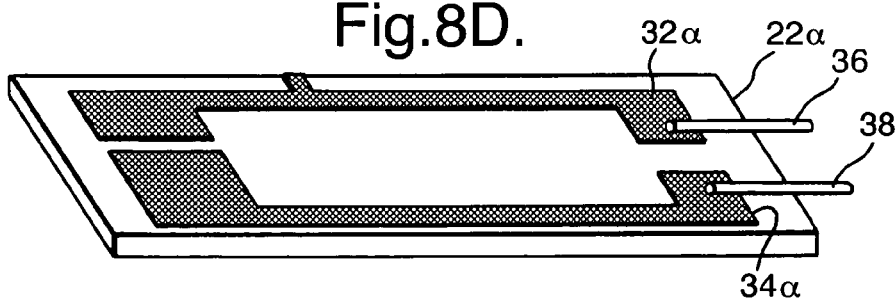

Next, as shown in FIG. 8C, platinum pastes 34α and 32α are applied to the surface of the solid electrolyte green sheet 22α by printing. The applied platinum pastes 34α and 32α will become the negative electrode 34a and the positive electrode 32a, respectively, through exposure to firing. Subsequently, as shown in FIG. 8D, the platinum wires 36 and 38 are placed at an end portion of the solid electrolyte green sheet 22; more specifically, at the portions of the platinum pastes 34α and 32α which will become the connection electrodes 34f and 32f through exposure to firing.

Figure 8E:
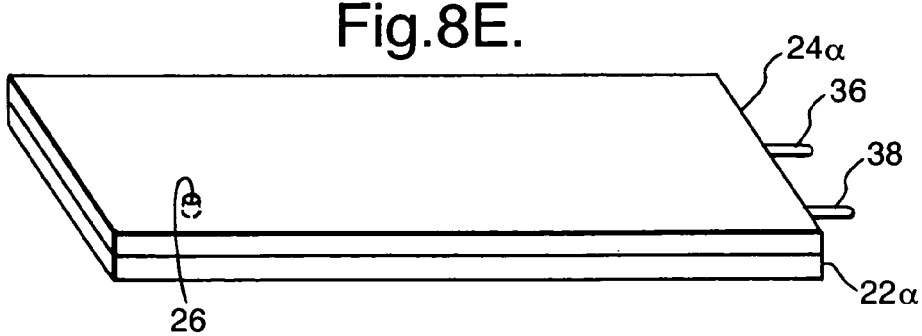

Subsequently, the solid electrolyte green sheet 24α of FIG. 5B is superposed on the solid electrolyte green sheet 22α of FIG. 8D (see FIG. 8E). The superposed solid electrolyte green sheets 22α and 24α are integrally fired at a temperature of 1500° C., thereby yielding the sensor element 20.

Next, a method for fabricating the ceramic heater 40 will be described with reference to FIG. 9.

Figure 9A:
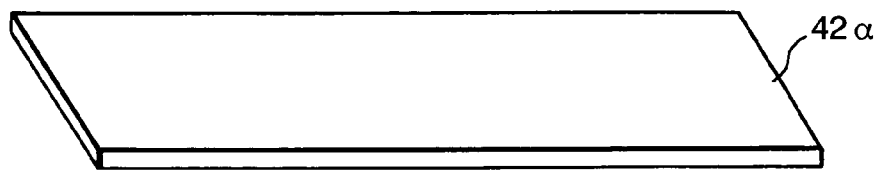
FIG. 9 including 9A, 9B, 9C and 9D and 9E are views showing a process for fabricating a ceramic heater of the flat limiting-current-type sensor.
Figure 9B:
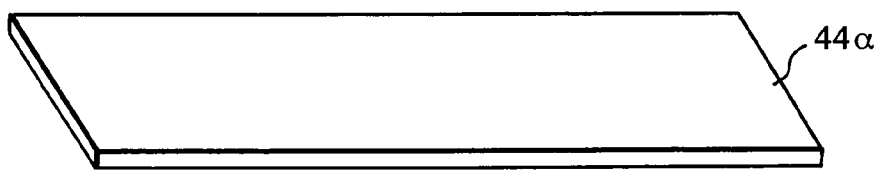
Figure 9C:
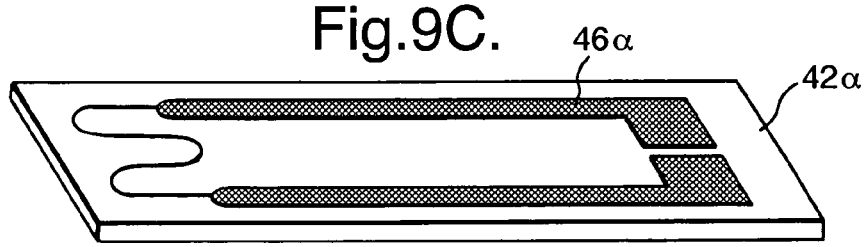

Alumina green sheets 42α and 44α are formed from a material which contains alumina powder as a main component (see FIGS. 9A and 9B). The alumina green sheets 42α and 44α will become the alumina substrates 42 and 44 through exposure to firing. Next, as shown in FIG. 9C, platinum paste 46α is applied to the surface of the alumina green sheet 42α by printing. The applied platinum paste 46α will become the heater electrodes 46a, 46b and 46c through exposure to firing. Subsequently, the platinum wires 56 and 58 are placed at an end portion of the alumina green sheet 42α; more specifically, at the portions of the platinum paste 46α which will become the heater connection electrodes 46e and 46f through exposure to firing.

Figure 9D:
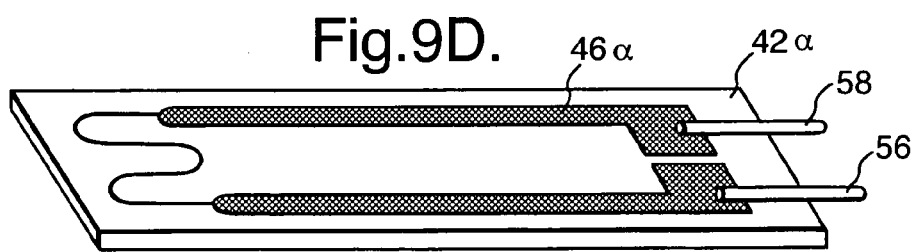
Figure 9E:
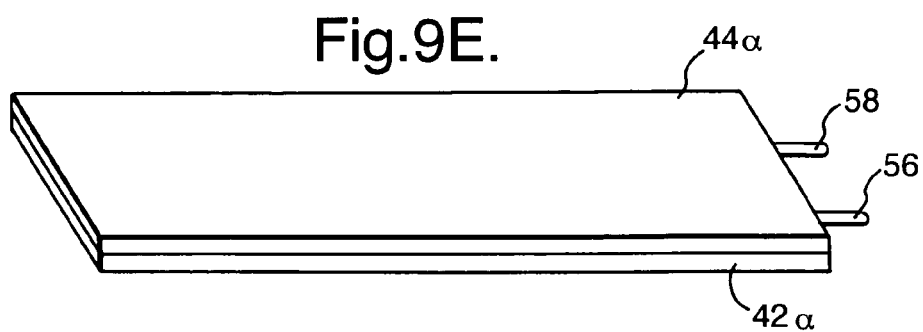

Subsequently, the alumina green sheet 44α of FIG. 9B is superposed on the alumina green sheet 42α of FIG. 9D (see FIG. 9E). The superposed alumina green sheets 42α and 44α are integrally fired at a temperature of 1500° C., thereby yielding the ceramic heater 40.

Finally, sealing glass is applied between the above-fabricated sensor element 20 and ceramic heater 40. The resulting assembly is heated at a temperature of about 800° C. so as to bond the sensor element 20 and the ceramic heater 40 together, thus yielding the flat limiting-current-type sensor 10.

Figure 10:
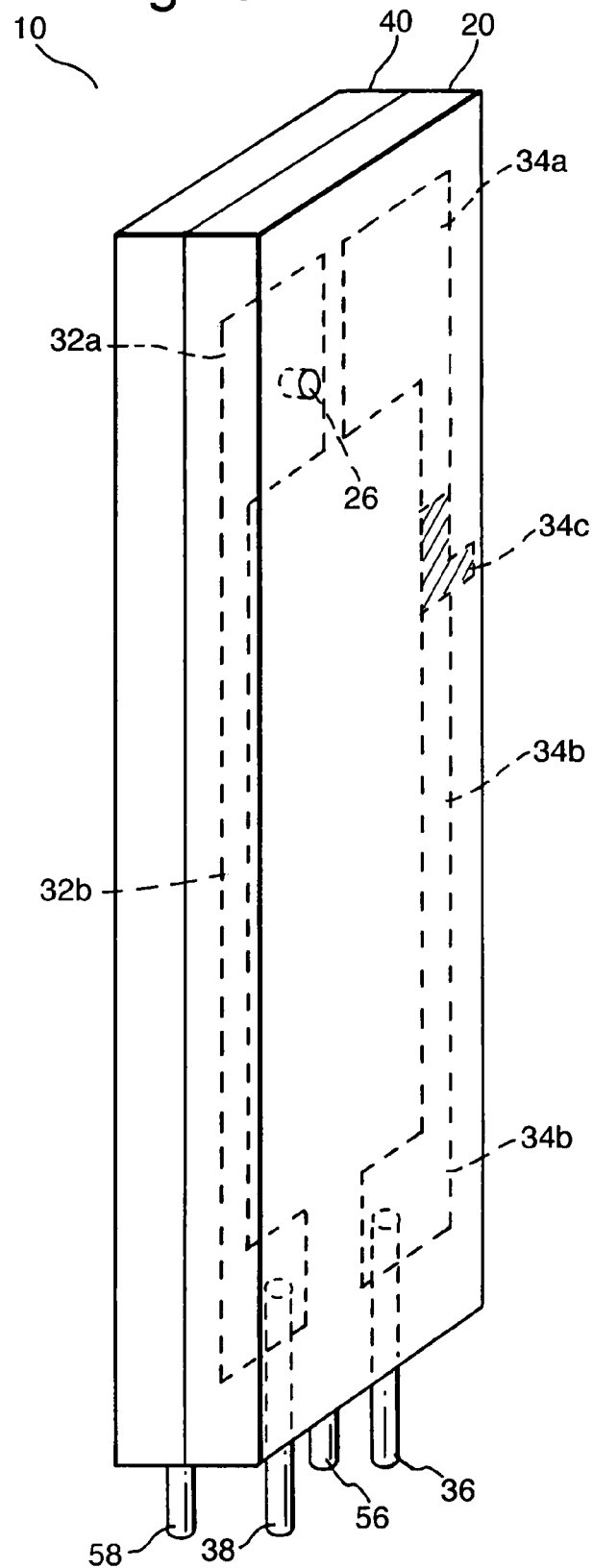
FIG. 10 is a perspective view of a flat limiting-current-type sensor according to a second embodiment of the present invention as viewed from the front side of the sensor.

A flat limiting-current-type sensor 10 according to a second embodiment of the present invention will next be described with reference to FIG. 10.

The flat limiting-current-type sensor of the second embodiment is configured in a manner similar to that of the flat limiting-current-type sensor of the first embodiment. However, the flat limiting-current-type sensor of the first embodiment is configured such that the area ratio between the negative electrode 34a and the positive electrode 32a is set to 1:2, since a voltage of 0.7 V is applied thereto for measurement of oxygen concentration. By contrast, the flat limiting-current-type sensor of the second embodiment is configured such that the area ratio between the negative electrode 34a and the positive electrode 32a is set to 2:1, is since a voltage of 1.8 V is applied thereto for use as a humidity sensor. As described above with reference to FIG. 5B, element resistance can be reduced to 81% of that of the conventional flat limiting-current-type sensor of FIG. 12B in which the negative electrode and the positive electrode assume the same area, thereby improving measurement accuracy.

Figure 11A:
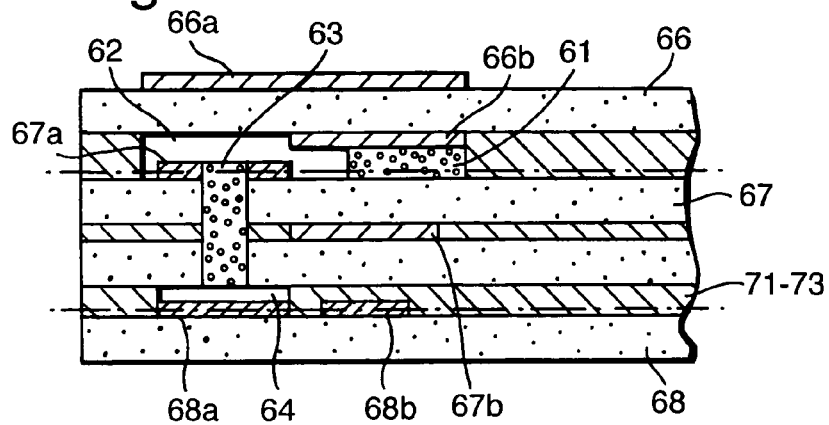
FIG. 11A is a longitudinal sectional view.
Figure 11B:
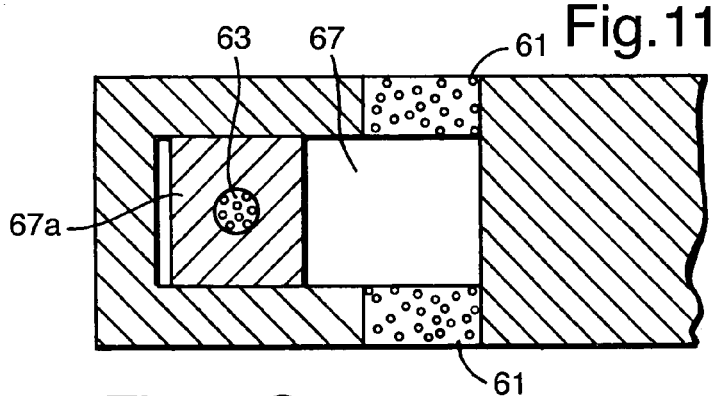
FIG. 11B is a plan view of a first measurement chamber portion.
Figure 11C:
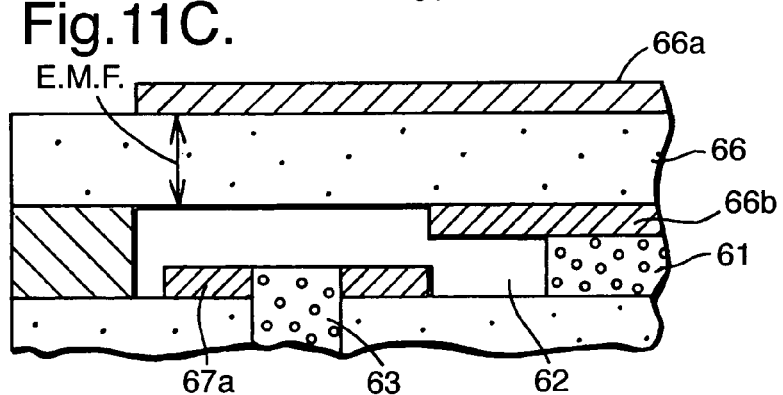
FIG. 11C is an enlarged sectional view of a main portion of the first measurement chamber.

A sensor according to a third embodiment of the present invention will next be described with reference to FIG. 11. The flat limiting-current-type sensors of the first and second embodiments are adapted to determine oxygen concentration or humidity, whereas the sensor of the third embodiment is adapted to determine the concentration of an oxygen-containing component of a measurement gas, for example, NOx concentration. FIG. 11A is a longitudinal sectional view of the sensor wherein a pair of negative and positive electrodes (68a and 68b) are formed different in area and in coplanar configuration on an oxygen ion conductive solid electrolyte substrate according to the third embodiment; FIG. 11B is a plan view of a first measurement chamber portion; FIG. 11C is an enlarged sectional view of a main portion of the first measurement chamber; and FIG. 11D is a view of a second measurement chamber as projected on a plane.

The sensor includes a first oxygen ion pump cell 66, an oxygen-concentration-measuring cell 67, and a second oxygen ion pump cell 68, which are sequentially arranged in layers. The first oxygen ion pump cell 66 includes a solid electrolyte layer and electrodes 66a (positive electrode) and 66b (negative electrode) provided on opposite sides of the solid electrolyte layer. The oxygen-concentration-measuring cell 67 includes a solid electrolyte layer and oxygen partial-pressure detection electrodes 67a and 67b provided on opposite sides of the solid electrolyte layer. The second oxygen ion pump cell 68 includes an oxygen ion conductive solid electrolyte layer and oxygen ion pump electrodes 68a and 68b provided on the same side of the solid electrolyte layer such that the oxygen ion pump electrode 68a is exposed to a second measurement chamber 64 and such that the oxygen ion pump electrode 68b is covered with an insulation layer 71-3. As shown in FIG. 11A, a first measurement chamber 62 is defined by the upper solid electrolyte layer of the first oxygen ion pump cell 66, the lower solid electrolyte layer of the oxygen-concentration-measuring cell 67, and lateral insulation layers. The second measurement chamber 64 is defined above the second oxygen ion pump cell 68 in a manner similar to that of the first measurement chamber 62. Further, first diffusion holes 61 and a second diffusion hole 63 are located apart from each other so as to serve as serial passageways for transmission of measurement gas from outside the sensor toward the electrode 68a via diffusion resistance of the passageways. The second diffusion hole 63 extends through the oxygen-concentration-measuring cell 67 and the solid electrolyte layer to thereby establish communication between the first and second measurement chambers 62 and 64. The second diffusion hole 63 is adapted to send gas which contains at least NOx and $O_2$, from the first measurement chamber 62 to the second measurement chamber 64 via the diffusion resistance.

An insulation layer of alumina is provided between the adjacent solid electrolyte layers. A heater layer is bonded to the sensor. Electrodes are connected to external devices, such as a power source, via leads formed between the adjacent layers. For example, referring to FIG. 11D, the electrodes 68a and 68b of the second oxygen ion pump cell 68 are electrically connected to leads 68c and 68d, respectively.

Figure 11D:
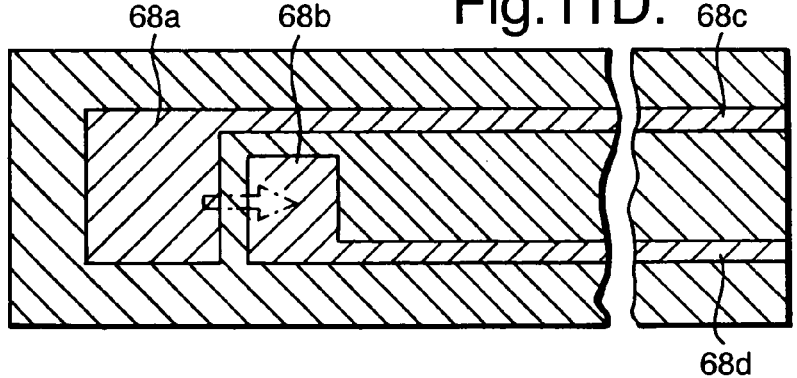
FIG. 11D is a view of a second measurement chamber as projected on a plane.

In this configuration shown in FIG. 11D, the oxygen ion pump electrodes 68a and 68b differ in area at least twofold. Accordingly, as in the case of the flat limiting-current-type sensors of the first and second embodiments, the element resistance of the second oxygen ion pump cell 68 that has negative and positive electrodes 68a, 68b in coplanar configuration is reduced. As a result, measurement accuracy in measuring a low current that flows between the electrodes 68a and 68b of the second cell 68, the current corresponding to an amount of oxygen dissociated from, e.g., NOx and pumped out as in the direction shown in a dotted arrow in FIG. 11D from the second cell 68, and thereby in determining the amount of NOx in the measurement gas based on the current, is improved.

A process for measuring the NOx concentration of a measurement gas, e.g., exhaust gas by referring to the NOx gas sensor as shown in FIG. 11, i.e., FIGS. 11A, 11B, 11C and 11D will next be described.

(a) Exhaust gas enters the first measurement chamber 62 through the first diffusion hole 61 having a gas diffusion resistance.

(b) The first oxygen ion pump cell 66 pumps out oxygen from the exhaust gas introduced into the first measurement chamber 62 until a portion of NOx decomposes ($2NO \rightarrow N_2 + O_2$). At this time, the first oxygen ion pump cell 66 is driven on the basis of signals output from the oxygen partial-pressure detection electrodes 67a and 67b so as to control the partial pressure of oxygen to a low level in the vicinity of the inlet of the second diffusion hole 63.

(c) A mixture of concentration-controlled $O_2$ gas and Nox gas diffuses from the first measurement chamber 62 to the second measurement chamber 64 through the second diffusion hole 63 having a gas diffusion resistance.

(d) The catalytic activity of the negative electrode 68a of the second pump cell 68 causes NOx gas contained in the second measurement chamber 64 to decompose into $N_2$ and $O_2$. The oxygen dissociated in the second chamber is pumped out through the second oxygen ion pump cell 68 since the second cell 68 is so formed to pump out oxygen under the voltage ($V_{p2}$) of about 0.15-1.1 volts applied across the second oxygen ion conductive cell electrodes 68a and 68b. At this time, since a pump current $I_{p2}$ flowing across the electrodes 68 a, 68b is linearly interrelated with NOx concentration of the measurement gas, the NOx concentration can be determined by measuring $I_{p2}$.

In such a sensor for the measurement of, e.g., a low NOx concentration of the gas, wherein voltage $V_{p2}$ applied to the second oxygen ion pump cell 68 is lower than 500 mV, the amount of oxygen decomposed from NOx decreases with a resultant decrease in pump current $I_{p2}$. As a result, the accuracy in determining the NOx concentration tends to be impaired. When $V_{p2}$ is in excess of 500 mV, $H_2O$ dissociation accelerates on the electrode 68a of the second oxygen ion pump cell 68. This is because $O_2$ generated through the dissociation of $H_2O$ causes pump current $I_{p2}$ to increase. As a result, the accuracy in determining NOx concentration tends to be impaired. Accordingly, voltage $V_{p2}$ applied to the second oxygen is preferably less than 500 mV, more preferably 200 to 480 mV, particularly preferably about 300 to about 450 mV in the case of NOx measurement of a gas containing oxygen and aqueous vapor. The present invention regarding the electrode area ratio of the negative electrode to positive electrode or the area ratio of the positive electrode to the negative electrode works especially good when the current across the electrodes is below 100 microamperes, or less than 10 microamperes, or even less than 1 microampere.

A better measurement accuracy is obtained when the area of the positive electrode is larger than that of the negative electrode in those cases of sensing dissociated oxygen by a low applied voltage below 1.1 volts when the measurement current is low as such. In sensing humidity in which a voltage of more than 1.1 volts is applied, better measurement accuracy is obtained when the negative electrode area is larger than the positive electrode.

It can be particularly effective, with embodiments of the invention, if the voltage applied between the positive and negative electrodes which are in a coplanar configuration is less than 0.5 V and the current between the electrodes is small, such as 10 microamperes. This improves the signal to noise ratio (S/N ratio) of the measurement signal, enabling greater accuracy to be achieved. For determining amounts of the order of parts per million (ppm) of a gas such as NOx, $CO_2$ and HC, the current is preferably 1 microampere or less. Embodiments of the present invention can achieve high accuracy under these conditions because of the lowering of the internal resistance of the electrolyte cell sensor.

An applicable solid electrolyte is, for example, a solid solution of zirconia and yttria or a solid solution of zirconia and calcia. Porous electrodes which are formed on opposite sides of a thin solid electrolyte layer by, for example, screen printing and sintering are preferably formed from platinum, rhodium, or an alloy thereof, such as a platinum alloy or a rhodium alloy. The first and second diffusion hole portions (gas diffusion means or gas diffusion passageways) are preferably formed from porous ceramic, such as porous alumina ceramic. A heater is preferably configured such that a heat-generating portion is formed from a composite material of ceramic and platinum or a platinum alloy and such that a lead portion is formed from platinum or a platinum alloy and the heater is provided on the sensor composed of the oxygen ion conductive solid electrolyte cells.

The configuration of the coplanar electrodes according to the invention as explained with the NOx sensor of the third embodiment may be applicable to a CO gas sensor and an HC gas sensor, etc., in which the negative and positive electrodes are provided on a coplanar same side of the solid electrolyte substrate including an oxygen ion conductive electrolyte.

The above embodiments are described while mentioning application of the configuration of the present invention to an oxygen sensor and an NOx sensor. However, the configuration of the present invention is not limited to such an application, but may be applied to other gas sensors, such as $H_2O$ sensors, $CO_2$ sensors, SOx sensors and HC sensors.

As described above, according to the present invention, the negative electrode and the positive electrode differ in area, thereby reducing element resistance therebetween and thus improving measurement accuracy for a given device. The invention enables a flat limiting-current-type sensor smaller in size than a conventional one to achieve a given measurement accuracy, thereby achieving a reduction in a flat sensor size and thus also decreasing the power consumption of a heater attached thereto.

While the invention has been described in detail and with reference to specific embodiments thereof, it will be apparent to one skilled in the art that various changes and modifications can be made therein without departing from the spirit and scope thereof.

What is claimed is:

1. An oxygen sensor for determining the oxygen concentration of a gas, comprising first and second chambers (62, 64) formed between first and second oxygen ion conductive cell substrates (66, 68) and first and second electrodes (68*a*, 68*b*) formed on the same plane of the second cell substrate (68), said first electrode (68*a*) being formed on an inside wall of the second chamber (64) and said second electrode (68*b*) being formed outside of the second chamber (64), wherein the area of the first electrode is at least twofold larger than that of the second electrode, and the sensor comprises means for applying an electric potential in the range of 0.2 V to 1.1 V between the first and second electrodes such that a pump current flows between the first and second electrodes when the sensor is used to determine the concentration of oxygen in a gas, said pump current being a measurement of oxygen concentration.

2. A humidity sensor for determining the humidity of a gas, comprising first and second chambers (62, 64) formed between first and second oxygen ion conductive cell substrates (66, 68) and first and second electrodes (68*a*, 68*b*) formed on the same plane of the second cell substrate (68), said first electrode (68*a*) being formed on an inside wall of the second chamber (64) and said second electrode (68*b*) being formed outside of the second chamber (64), wherein the area of the first electrode is at least twofold larger than that of the second electrode, and the sensor comprises means for applying an electric potential in the range of 1.1 V to 2.5 V between the first and second electrodes such that a pump current flows between the first and second electrodes when the sensor is used to determine the humidity of a gas, said pump current being a measurement of humidity.

3. An oxygen sensor for determining the oxygen concentration as a component of a gas containing NOx, comprising first and second chambers (62, 64) formed between first and second oxygen ion cell substrates (66, 68) and first and second electrodes (68*a*, 68*b*) formed on the same plane of the second cell substrate (68), said first electrode (68*a*) being formed on an inside wall of the second chamber (64) and said second electrode (68*b*) being outside of the second chamber (64), wherein the area of the first electrode is at least twofold larger than that of the second electrode, and the sensor comprises means for applying an electric potential in the range of 0.2 V to less than 0.5 V such that a pump current flows between the first and second electrodes when the sensor is used to determine oxygen concentration as a component of a gas containing NOx, said pump current being a measurement of oxygen concentration.

4. The oxygen sensor as claimed in claim 3, wherein a pump current of less than 10 microamperes flows between the first and second electrodes when an electric potential in the range of 0.2 V to less than 0.5 V is applied across the first and second electrodes.

5. A sensor for detecting the amount of a gas, comprising:

a first oxygen ion pump cell (66), an oxygen-concentration-measuring cell (67), and a second oxygen ion pump cell (68), which are sequentially arranged over each other;

the first oxygen ion pump cell (66) including a first solid electrolyte layer and electrodes (66a) and (66b) provided on opposite sides of the first solid electrolyte layer;

the oxygen-concentration-measuring cell (67) including a second solid electrolyte layer and oxygen partial-pressure detection electrodes (67a) and (67b) provided on opposite sides of the second solid electrolyte layer;

the second oxygen ion pump cell (68) including a third oxygen ion conductive solid electrolyte layer and oxygen pump electrodes (68a) and (68b) provided on the same side of the third oxygen ion conductive solid electrolyte layer;

a first measurement chamber (62) defined by the first oxygen ion pump cell (66);

a second measurement chamber (64) defined by the second oxygen ion pump cell (68);

first and second diffusion holes (61) and (63) located apart from one another and serving as serial passageways for transmission of measurement gas from outside of the sensor toward the electrode (68a) via diffusion resistance, said second diffusion hole (63) extending through the oxygen-concentration-measuring cell (67) and the second solid electrolyte layer to establish communication between the first and second measurement chambers (62) and (64); and said oxygen ion pump electrodes (68a) and (68b) differing in area by at least twofold.

6. A sensor element (20) comprising a first solid electrolyte substrate (22), a second solid electrolyte substrate (24) and a negative electrode (34a) and positive electrode (32a) sandwiched between said first and second solid electrolyte substrates, said negative and positive electrodes being disposed on the same side of said first solid electrolyte substrate (22), the sensor element further comprising a gas diffusion portion (34c) for introducing a gas to be measured into the negative electrode (34a) and a gas outlet hole (26) formed through the second solid electrolyte substrate (24) 50 as to expose a portion of the positive electrode (32a) allowing oxygen to be released from the positive electrode (32a) to an exterior of the sensor element (20), wherein the area of said negative electrode (34a) and the area of said positive electrode (32a) differ by at least two fold.

* * * * *